United States Patent [19]

Pujado

[11] Patent Number: 4,761,504

[45] Date of Patent: Aug. 2, 1988

[54] INTEGRATED PROCESS FOR HIGH OCTANE ALKYLATION AND ETHERIFICATION

[75] Inventor: Peter R. Pujado, Palatine, Ill.

[73] Assignee: UOP Inc., Des Plaines, Ill.

[21] Appl. No.: 947,009

[22] Filed: Dec. 29, 1986

[51] Int. Cl.$^4$ .......................... C07C 2/62; C07C 41/06
[52] U.S. Cl. ...................................... 568/697; 585/331
[58] Field of Search .......................... 568/697; 585/331

[56] References Cited

U.S. PATENT DOCUMENTS

| | | | |
|---|---|---|---|
| 3,726,942 | 4/1973 | Louder | 568/697 |
| 4,195,191 | 3/1980 | Boney | 585/706 |
| 4,219,678 | 8/1980 | Obenaus et al. | 568/697 |
| 4,220,806 | 9/1980 | Mikulicz et al. | 585/716 |
| 4,270,929 | 6/1981 | Quang Dang Vu et al. | 585/331 |
| 4,282,389 | 8/1981 | Droste et al. | 568/697 |
| 4,324,924 | 4/1982 | Torck et al. | 568/697 |
| 4,371,718 | 2/1983 | Hutson, Jr. | 568/697 |
| 4,544,777 | 10/1985 | Hutson, Jr. et al. | 568/697 |
| 4,575,566 | 3/1986 | Vora | 568/697 |
| 4,579,998 | 4/1986 | Hutson, Jr. | 585/716 |
| 4,581,474 | 4/1986 | Hutson, Jr. et al. | 568/697 |

FOREIGN PATENT DOCUMENTS

| | | | |
|---|---|---|---|
| 103870 | 3/1984 | European Pat. Off. | 568/697 |
| 1369889 | 10/1974 | United Kingdom . | |

OTHER PUBLICATIONS

Herwig, J. et al., "New Low Energy Process for MTBE and TAME," *Hydrocarbon Processing*, pp. 86–88.

Obenaus, Fritz Dr., "Huls-Process: Methyl Tertiary Butylether," AIChe 85th National Meeting, Philadelphia, Jun. 4–8, 1978.

*Primary Examiner*—Howard T. Mars
*Attorney, Agent, or Firm*—Thomas K. McBride; John F. Spears, Jr.

[57] ABSTRACT

A process is disclosed for the simultaneous alkylation of light hydrocarbons to produce gasoline blending components and the etherification of an isoolefin to produce an ether. The etherification zone effluent stream contains normal olefins and isoparaffins consumed in an acid-catalyzed alkylation zone. The etherification zone effluent stream is separated in a fractionation column in a manner which provides a small amount of ether in the hydrocarbon-rich overhead stream. The presence of the ether in the acid-catalyst is beneficial to the alkylation reaction by providing a higher octane number product.

8 Claims, 1 Drawing Sheet

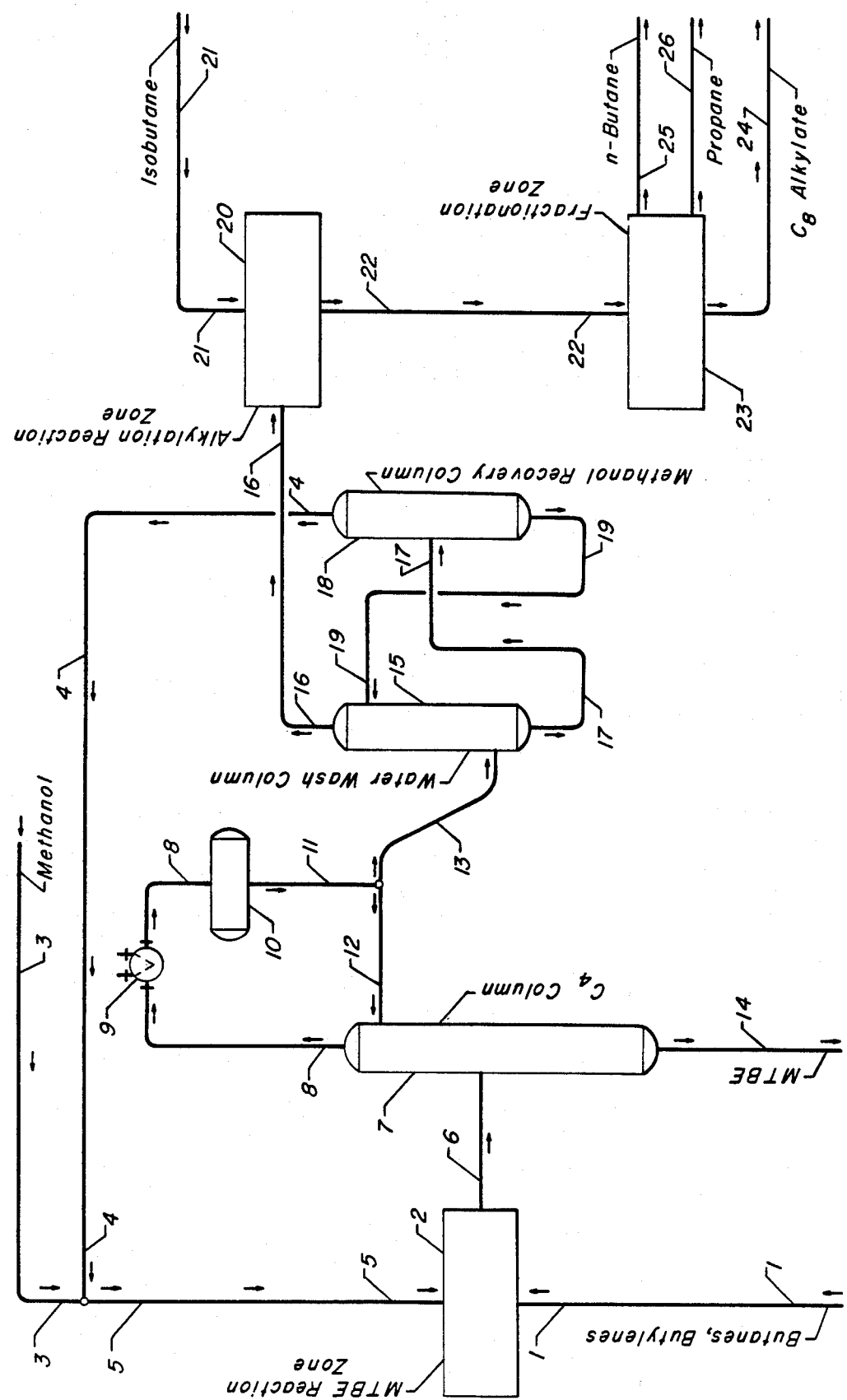

INTEGRATED PROCESS FOR HIGH OCTANE ALKYLATION AND ETHERIFICATION

FIELD OF THE INVENTION

The invention is a hydrocarbon conversion process in which specific hydrocarbons present in a $C_4$ feed stream are converted to a $C_5+$ ether and a high octane number alkylate suitable for use as a motor fuel blending component. The invention therefore relates to the general area of petroleum refining processes used to transform light hydrocarbons into gasoline components. The invention is specifically directed to a process for the production of light ethers which may be employed as octane number enhancement agents in gasoline. The invention is also directly related to the alkylation process often referred to as motor fuel alkylation or HF alkylation which is employed within petroleum refineries to convert $C_3$–$C_5$ hydrocarbons into $C_8$ acyclic hydrocarbons by the alkylation of an isoparaffin with an olefin.

PRIOR ART

The subject invention builds upon two processes, etherification and alkylation, which are well-developed and are utilized commercially in a number of petroleum refineries and petrochemical installations. Both etherification and alkylation processes are available for licensing from a number of companies.

The etherification process most relevant to the subject invention is the production of methyl tertiary butyl ether (MTBE) by the reaction of isobutylene with methanol. Information about one etherification process and a simplified flow diagram is presented in the article starting at page 86 of the June 1984 edition of *Hydrocarbon Processing*. A description of another etherification process is presented in the paper presented at the AICHE 85th National Meeting, June 4–8, 1978 by Fritz Obenaus and Wilhelm Droste, entitled, "Huls-Process: Methyl Tertiary Butyl Ether". U.S. Pat. Nos. 4,219,678 and 4,282,389 are also believed pertinent for their teaching in regard to the operation of the etherification zone, possible feed streams to this zone, and in particular the processing of the effluent stream removed from the etherification reaction zone. These references illustrate the passage of the etherification reaction zone effluent stream into the water wash column for the recovery of methanol, followed by the recovery of methanol from the water wash stream. The recycling of methanol to the reaction zone is also disclosed in these references. Further, the non-patent references illustrate that the etherification zone effluent stream may be fractionated in different flow schemes to yield different product streams. These references also indicate that the reaction zone effluent itself may be withdrawn as a bottoms-stream containing a mixture of MTBE and $C_4$ hydrocarbons suitable for use as a gasoline blending stream. It is believed, however, that in all of these references substantially all of the MTBE is intentionally removed as a bottoms stream of the first fractionation column which receives the effluent stream of the etherification zone. That is, heretofore MTBE has not been removed overhead with the $C_4$ hydrocarbons, often referred to as the $C_4$ raffinate, which are discharged from the process or subjected to further processing.

Alkylation processes for the conversion of $C_4$ olefins and paraffins into a mixture of $C_8$ hydrocarbons referred to as alkylate are also widely known in the art. U.S. Pat. Nos. 4,195,191 to W. G. Boney; 4,220,806 to M. Z. Mikulicz et al.; and 4,579,998 issued to T. Hudson, Jr. are pertinent for their showing of the state of the art of HF alkylation of light paraffins to produce motor fuel alkylate. These references describe current operating procedures, reaction conditions, catalysts, reactants and product recovery flow schemes.

As both the etherification processes for the production of MTBE and the alkylation processes for the production of motor fuel alkylate are often performed at the same location, that is within the same refinery, and for the similar purpose of gasoline production those skilled in the art have focused attention on the integration of these two process units. For instance, U.S. Pat. No. 4,371,718 issued to T. Hudson, Jr. describes the operation of an etherification process producing methyl tertiary ether and the treating of the $C_4$ effluent or raffinate from the etherification reactor prior to its passage into an HF alkylation unit. U.S. Pat. No. 4,581,474 also issued to T. Hudson, Jr. et al. illustrates an integrated process for the production of MTBE and alkylate motor fuel. A $C_4$ olefin feed stream and a methanol feed stream are reacted in the MTBE plant to produce MTBE which is withdrawn. The remaining $C_4$ hydrocarbons are subjected to an absorption step to remove butene-2. The remaining hydrocarbons are subjected to isomerization to produce butene-2 or to produce isobutylene. The isobutylene may be recycled to the MTBE plant, and the butene-2-containing isomerate is used as a desorbent to pass the normal butenes into an HF alkylation plant. U.S. Pat. No. 4,544,777 also issued to T. Hudson, Jr. describes the heat integration which may be achieved when an MTBE etherification zone is combined with an HF alkylation zone to produce motor fuel alkylate. In these three highly pertinent references it is believed that all of the MTBE produced in the etherification zone and charged to the etherification zone products separation fractionation column is withdrawn as a bottoms product of the fractionation column.

U.S. patent application Ser. No. 764,707 filed 8-12-85 by T. Imai et al. is believed relevant for its teaching of the beneficial presence of MTBE in an HF alkylation reaction zone. The MTBE and the HF combine to form a single liquid phase catalyst which produces a higher octane number product than is achieved through the use of HF alone.

BRIEF SUMMARY OF THE INVENTION

The invention provides an improved method of integrating a process for the production of an ether, such as MTBE, with an alkylation unit in which motor fuel alkylate is produced. The invention provides a straightforward method of charging an ether to the alkylation zone for the beneficial purpose of increasing the octane number of the product alkylate recovered from the alkylation zone. This beneficial effect is achieved by operating the fractionation column which receives the etherification zone effluent stream in such a manner that the net overhead stream of the fractionation column contains MTBE in an amount sufficient to maintain the desired MTBE concentration in the alkylation zone catalyst.

One embodiment of the invention may be broadly characterized as a process for the production of a branched chain acyclic hydrocarbon by the alkylation reaction of a normal olefin and an isoparaffin, which process comprises the steps of contacting a mixture of hydrocarbons comprising a normal olefin, an isoolefin and an isoparaffin wtih an aliphatic alcohol in the presence of an etherification catalyst and producing an etherification zone effluent stream which comprises a $C_4$-plus ether, the normal olefin and the isoparaffin; separating the etherification zone effluent stream within a fractionation zone into a net bottoms stream which is rich in the ether and a net overhead stream which comprises essentially all of the $C_4$ hydrocarbons present in the etherification zone effluent stream, with the net overhead stream also containing sufficient ether to have an ether concentration of at least 0.3 mole percent; passing the net overhead stream into an alkylation zone in which the isoparaffin and the normal olefin are reacted in the presence of a mineral acid and the ether to produce a $C_7$-plus acyclic product hydrocarbon; and recovering the product hydrocarbon.

BRIEF DESCRIPTION OF THE DRAWING

The Drawing is a simplified process flow diagram illustrating the separation of the etherification zone effluent stream in a fractionation column 7, with essentially all of the $C_4$ hydrocarbons and a discrete amount of MTBE emerging as the net overhead stream of line 13 which is passed into the alkylation zone 20 after passing through the water wash column 15 for the removal of methanol.

DETAILED DESCRIPTION

Many large scale alkylation units for the production of high octane motor fuel blending components are actively operated worldwide. In these motor fuel alkylation units an isoparaffin, normally isobutane, is reacted with a normal olefin, preferably normal butene, to produce $C_8$ hydrocarbons. The resulting acyclic highly branched hydrocarbons have a high octane number and may be used in blending a superior quality gasoline. Methyl tertiary butyl ether (MTBE) is being used increasingly as an octane booster in gasolines. Such octane boosters are being employed to satisfy the octane demands of more modern automotive engines and to eliminate the effects of removing certain lead-containing compounds from gasoline as mandated to produce lead-free gasoline. Both the alkylation and the etherification processes therefore find great utility in the petroleum refining industry.

It has been discovered that employing a catalyst system consisting of HF and a refractory ether, preferably MTBE, results in a motor fuel alkylation unit producing a higher octane number product. The octane number improvement due to the use of this new catalyst system may be on the order of 1½ to 2 octane numbers. This is a very significant increase in octane which may be achieved with little increased cost. It is an objective of the subject invention to provide a method of integrating etherification and alkylation zones in a motor fuel producing complex. It is a specific objective of the subject invention to provide a method of establishing and maintaining a desired concentration of MTBE or other ethers in the alkylation catalysts employed in a motor fuel alkylation hydrocarbon conversion process.

In the subject invention these objectives are achieved by fractionating the effluent of the etherification zone in a novel manner which results in the concentration of the unreacted $C_4$-minus hydrocarbons and a definite quantity of the product ether into a net overhead stream removed from the fractionation zone. The stream containing the $C_4$-minus unreacted hydrocarbons is normally referred to as the etherification zone raffinate stream. The remainder of the ether is withdrawn from the column in the conventional manner in a net bottoms product. The ether-containing hydrocarbon stream removed as the overhead product of the fractionation column is then treated as desired as for the removal of methanol and is passed directly into the alkylation reaction zone. In this manner both MTBE and the light hydrocarbon reactants consumed in the alkylation zone are fed directly into the alkylation zone as the components of a single stream.

The Drawing illustrates a preferred embodiment of the invention. This presentation of a description of one embodiment of the invention is not intended to preclude from the scope of the invention those other embodiments set out herein or which are the result of the normal and expected modification of those embodiments. Referring now to the Drawing, a feedstream comprising an admixture of essentially all of the butanes and butenes including isobutane, normal butane, butene-1, butene-2 and isobutylene is charged to the MTBE reaction zone 2 through line 1. In this etherification zone, the isobutylene present in the stream of line 1 reacts with methanol passed into the process via lines 3 and 5 and recycled methanol from line 4. The methanol selectively reacts with the isobutylene present in the feed stream of line 1. The result is the production of MTBE which is discharged from the reaction zone 2 through line 6 in an effluent stream which also contains unconsumed methanol and the unreacted $C_4$ hydrocarbons which are charged to the etherification zone through line 1.

The etherification zone effluent stream is passed into an intermediate point of a fractionation column 7 referred to commonly as a $C_4$ column. This fractionation column is designed and operated at conditions effective to separate the entering chemical compounds into a net bottoms stream withdrawn through line 14 and a net overhead vapor stream removed through line 8. The net bottoms stream of line 14 should be essentially free of $C_4$ hydrocarbons. This stream will be rich in MTBE and may contain some methanol and TBA. The TBA (tertiary butyl alcohol) would be due to the presence of water in the feed methanol or in the recycled methanol of line 4. The MTBE may be passed to further purification zones such as additional fractional columns or may be used directly as a motor fuel blending component. This separation is achieved through the use of a reboiling means not shown located at the bottom of the fractionation column 7.

The overhead vapor of the fractionation column is carried by line 8 through the overhead condenser 9 and then into the overhead receiver 10. Essentially all of the material flowing through line 8 should be condensable at normal operating conditions, resulting in the accumulation of a liquid phase material in the receiver 10. This overhead liquid is removed through line 11 and divided into a first portion which is passed as reflux into the top of the fractionation column 7 through line 12 and a second portion which is withdrawn through line 13 as the net overhead stream of the fractionation column. The overhead stream of line 13 will contain the majority of the methanol originally present in the reaction zone effluent stream of line 6.

The net overhead stream of the fractionation column is passed into a lower point of a water wash column 15. The hydrocarbon phase of line 13 ascends upward through the water wash column countercurrent to a descending stream of water charged to a top portion of the water wash column from line 19. During this upward passage, methanol present in the net overhead stream transfers to the aqueous phase present in the water wash column. In this way, methanol originally present in the etherification zone effluent stream is recovered.

A liquid phase water stream containing dissolved methanol is removed from the bottom of the water wash column through line 17 and passed into an intermediate point of a methanol recovery column 18. Column 18 is a fractionation column heated through the use of a reboiling means not shown and designed and operated to effect a separation of the entering water and methanol into a net overhead stream removed through line 4 having a very high concentration of methanol and a water stream removed through line 19 which is essentially free of methanol. The bottoms stream of the methanol recovery column is then passed into the top of the water wash column to complete the circuit. This removal of methanol is desirable to reduce the required makeup methanol feed rate to the etherification zone and also to prevent the normally undesired entrance of methanol into the alkylation zone. In many instances the passage of methanol into the alkylation zone will result in the breakdown of the methanol and the release of water. The water would normally dilute the mineral acid utilized as catalyst within the alkylation zone and can lead to substantial corrosion problems. It is therefore normally undesired to pass any alcohol into the alkylation reaction zone.

The hydrocarbonaceous effluent of the water wash column withdrawn through line 16 will comprise the $C_4$ hydrocarbons (normal butane, butene-2, butene-1, and isobutane) originally present in the etherification zone effluent stream. The hydrocarbons will be saturated with water as they emerge from the water wash column. This water must be removed as by the use of regenerable adsorbents such as alumina prior to passage into the alkylation zone. It will also contain the small but definite quantity of MTBE intentionally caused to be present in the overhead stream of the $C_4$ column. This admixture of chemical compounds is passed into the alkylation zone 20 through line 16. A methanol depleted and ether-containing $C_4$ raffinate stream is thereby passed into the alkylation reaction zone and brought into contact with an alkylation catalyst. The preferred alkylation catalyst comprises an admixture of HF and MTBE. In addition to the $C_4$ raffinate stream a supplemental feed stream comprising isobutane carried by line 21 will normally be charged to the alkylation reaction zone to provide the desired isobutane to normal butene ratio.

The contacting of the feed materials in one or more reaction stages results in the combination of the isobutane with the normal butenes and the production of an alkylation reaction zone effluent stream carried by line 22 which comprises an admixture of unconverted $C_4$ hydrocarbons, product $C_8$ hydrocarbons, and other hydrocarbons which may have entered the reaction zone or which like propane are produced in the reaction zone as by-products of the alkylation reaction including small amounts of $C_7$ or $C_9$ plus hydrocarbons. This alkylation reaction zone effluent stream is passed through line 22 into a fractionation zone 23. As is illustrated and described in the previously cited references the fractionation zone may take on several forms. Normally, two or more fractionation columns are employed to separate the entering hydrocarbons into a $C_8$ product stream removed through line 24, a stream of unreactive normal butane removed from the process through line 25 and a light hydrocarbon stream comprising propane discharged from the process through line 26.

In the embodiment illustrated in the drawing, methanol present in the overhead stream of the fractionation column is removed from this hydrocarbonaceous stream by countercurrent extraction with water. This action is performed in a water wash column with a methanol-containing extract stream being removed from the bottom of the water wash column and passed into a fractionation column. In the fractionation column, methanol is recovered for recycling to the reaction zone by fractionation. The use of such methanol washing columns is well-known in the art as they are employed on many commercial units and are described in many references. The water wash column is typically operated at a positive pressure greater than about 70 kPa g to maintain liquid phase conditions. Elevated pressures above that necessary to maintain liquid phase conditions are not required or desired. The temperature of the aqueous stream descending through the rising hydrocarbons would normally be between 50° to 150° F. (10° to 65° C.) The water wash column itself may be a packed or trayed column preferably providing necessary agitation and contacting to provide at least 5 equivalent contacting stages for the desired extraction. As is also known in the art, alternative arrangements may be used to remove methanol from the net overhead stream of the fractionation column. For instance, previously cited U.S. Pat. No. 4,371,718 illustrates the use of solid bed adsorption to remove the menthanol. The overhead stream is passed through one bed of adsorbent while a second bed is undergoing regeneration. A suitable adsorbent is activated alumina maintained at a temperature below 100° F. (38° C.) and at a positive atmospheric pressure above about 150 kPa g and ranging up to about 1400 kPa g. The hydrocarbons should be passed through the alumina at a liquid hourly space velocity less than 1.0 but preferably greater than 0.2. The activated alumina may be regenerated through the use of a high temperature desorption stream preferably having a temperature above about 340° F. (171° C.). Molecular sieves and other zeolitic materials may also be employed as the adsorbent.

The design and/or operation of the fractionation zone used to separate the etherification zone effluent stream will require some modification from that used in the prior art. These changes are necessitated by the lifting of the ether into the net overhead stream which is accomplished in this fractionation zone but which is not performed in the prior art processes. The lifting of the heavier ether component into the overhead stream will require either an increase in the temperature or a decrease in the pressure or both as compared to the prior art operating conditions. A customarily designed single fractionation column having standard design sieve trays is suitable for the separation of the etherification zone effluent stream. The design of the fractionation zone may require adjustment to compensate for the use of a single or a plural stage etherification reaction zone. For instance, if the process utilizes two separate etherification reaction zones operated in series with intermediate separation of some or all of the ether produced in the first stage the composition of the effluent stream of the second stage will be quite different from that expected in the normal situation of a single stage etherification zone effluent stream being injected into the fractionation column. In this instance, the concentration of the product ether in the etherification zone effluent stream from the second stage will be reduced as compared to the situation where there is no prior upstream separation of ether.

Etherification processes have been constructed and proposed for the production of a variety of ethers. These ethers are themselves useful end products but alternatively can be used as feed compounds in processes for producing other valuable chemical compounds. For instance, plans have been announced to produce pure isobutylene for the manufacture of polyisobutylenes and tert-butyl-phenol by first producing methyl tertiary butyl ether (MTBE) and then cracking the MTBE to yield isobutylene and methanol, which is recycled. Large amounts of MTBE are also being produced for use as anti-knock compounds in lead-free gasoline. Etherification processes therefore find utility in both the petrochemical and petroleum refining industries.

The majority of the description of the invention is presented in terms of the reaction of isobutylene with methanol to form MTBE since these are the preferred feed materials and the commercially predominant reaction. However, it is not intended to thereby lessen the scope of the inventive concept, which may be applied in the production of other refractory ethers when a beneficial effect results from the passage of a controlled amount of the refractory ether into an alkylation zone. The inventive concept may therefore be applied in general to the reaction of isoolefins having less than six carbon atoms per molecule with water-soluble alcohols which preferably have less than four carbon atoms per molecule. The next preferred alcohol after methanol is ethanol but other alcohols such as propanols, ethylene glycol or propylene glycol can also be consumed in the process. The subject process may therefore be employed in the production of a wide variety of ethers other than MTBE including methyl tertiary amyl ether, ethyl tertiary amyl ether, and ethyl tertiary butyl ether. The subject process is, however, limited to the production of refractory ethers. The term "refractory" is intended to indicate ethers which do not quickly break down or hydrolyze in the presence of HF and which therefore remain admixed with the HF as a catalyst component.

The ethers are produced by the reaction of the alcohol and the isoolefin in an etherification zone. The ethers are then separated from unreacted hydrocarbons, water and unreacted alcohol to yield the ether product stream. In the case of MTBE production, the unreacted hydrocarbons include normal butenes, since these compounds do not react with the alcohol. Also normally present is a sizable amount of isobutane remaining from the isobutane present in the etherification zone feed stream. These unreacted hydrocarbons are withdrawn from the fractionation facilities used to recover the ether as a separate hydrocarbonaceous overhead stream as described above. Other components of the overhead stream include smaller amounts of various oxygenates such as the product ether, the feed alcohol and oxygen-containing reaction by-products, such as dimethyl ether, resulting from side reactions.

In the subject invention the $C_4$ hydrocarbon-rich overhead stream is passed into an HF alkylation zone for the production of $C_8$ alkylate by the reaction of normal butenes with isobutane. This process is described in detail below. It is undesirable to pass methanol into an HF alkylation zone since it accumulates in the HF and is very difficult to remove from the process. As indicated above, methanol also results in the undesired production of water. It is also undesirable to allow light oxygenates such as dimethyl ether (DME) to enter an HF alkylation zone. DME is essentially a noncondensable material at the conditions maintained in the alkylation zone. It must therefore be removed by venting HF vapor to an off-gas scrubbing zone. This is an inherently dangerous and costly procedure, which generates hazardous waste disposal problems.

The etherification zone may take many different forms but is preferably similar to that described in U.S. Pat. No. 4,219,678 and shown in the previously cited paper. In this instance the isobutane or other isoolefin, a feed stream of methanol or other feed alcohol, and a recycle stream containing the methanol are passed into the reaction zone in which they are contacted with an acidic catalyst while maintained at etherification conditions. A wide range of materials is known to be effective as etherification catalysts for the preferred reactants including mineral acids such as sulfuric acid, boron trifluoride, phosphoric acid on kieselguhr, phosphorus-modified zeolites, heteropolyacids, and various sulfonated resins. The use of a sulfonated solid resin catalyst is preferred. These resin-type catalysts include the reaction products of phenol-formaldehyde resins and sulfuric acid and sulfonated polystyrene resins including those cross-linked with divinylbenzene. Further information on suitable etherification catalysts may be obtained by reference to U.S. Pat. Nos. 2,480,940; 2,922,822; and 4,270,929 and the previously cited etherification references.

A broad range of etherification conditions include a superatmospheric pressure sufficient to maintain the reactants as a liquid phase, generally below about 200 psig (1380 kPa g), and a temperature between about 30° and about 100° C. A preferred temperature range is from 50° to 100° C. The reaction rate is normally faster at higher temperatures but conversion is more complete at lower temperatures. High conversion in a moderate volume reaction zone can therefore be obtained if the initial section of the reaction zone, e.g. the first two-thirds, is maintained above 70° C. and the remainder of the reaction zone is maintained below 50° C. This may be accomplished most easily using two reactors in series but the actual reactor configuration ultimately will depend on the feed composition, the desired extent of the etherification reaction and economic considerations. The ratio of feed alcohol to isoolefin should normally be maintained in the broad range of from 1:1 to 2:1. With the preferred reactants good results are achieved if the ratio of methanol to isobutene is between 1.1:1 and 1.5:1. An excess of methanol above that required to achieve satisfactory conversion at good selectivity should be avoided.

As used herein, the term "alkylation reaction zone" is intended to indicate a sequence of processing equipment in which the entering reactants are contacted with an alkylation catalyst maintained at alkylation-promoting conditions including one or more reaction vessels and the required equipment for the separation and recovery of the resultant alkylate from process streams recirculated within the reaction zone. It is preferred that the alkylation reaction zone contains no fractionation columns other than that used for catalyst regeneration. The preferred alkylation reaction is the reaction between isobutane and normal butenes to produce high octane $C_8$ hydrocarbons useful as gasoline blending components. Other alkylation reactions can also be performed, but the alkylation zone will be described in terms of the preferred reaction.

The alkylation reaction is preferably promoted by the presence of a mineral acid-catalyst such as hydrofluoric acid, sulfuric acid or phosphoric acid with hydrofluoric acid being preferred. These acids are preferably maintained in a liquid phase containing a minimum of water to reduce corrosion problems. The maximum amount of water normally allowed in the acid is about 5 wt. %. When fresh acid is charged to a plant, it is normally very dry and contains about 0.5 wt. % water or less. The catalyst will also comprise between 1.5 and 15.0 mole percent of the ether produced in the upstream etherification zone.

Alkylation conditions in general include a pressure sufficient to maintain the hydrocarbons and acid in a liquid phase, with a general range being from about 20 to about 500 psig (138–3450 kPa g), and a more preferred range being from 100 to about 250 psig (690–1724 kPa g). It is preferred that the pressure within the reactant-catalyst contacting vessel be approximately 150 psig (1034 kPa g) and essentially "floats" on the pressure maintained in the downstream fractionation zone. Although the desired alkylation reaction may be performed at temperatures from below −18° to about 90° C., it is preferred to operate the commercially prevalent isoparaffin-olefin alkylation process in the range of from about 10° to about 60° C., with 32° C. being a representative and particularly preferred operating temperature.

Typical operating conditions in the alkylation zone include a high ratio of the concentration of the paraffinic or other alkylatable material to the concentration of the olefinic material in order to produce a high quality alkylate by encouraging monoalkylation instead of polymerization. A broad range of this ratio is from about 6 to about 20 with a preferred operating range being from 8 to 12. A second ratio which varies in competing alkylation processes is the ratio of the acid to the hydrocarbons in the total emulsion formed, that is, the ratio in the material charged to the mixing zone or reaction point. This ratio may vary widely from a high of about 10:1 to a low of about 0.5:1, but it is preferred that the subject process is operated at an acid to hydrocarbon ratio of about 2:1.

There are a great number of olefin-isoparaffin alkylation methods known to those skilled in the art. The great majority of these processes will operate within the range of alkylation conditions set out above. They could however have substantial differences in equipment and flow paths used in performing the alkylation. These variations are attempts to obtain optimum quality akylate by varying the method of contacting the monoolefin with the isoparaffin. Since this reaction occurs very rapidly, and also because hydrofluoric acid will catalyze the polymerization of the monoolefin, the standard alkylation methods consist of either first admixing acid-free streams of olefin and isoparaffin to form a reactant mixture which is then admixed with the hydrofluoric acid-ether catalyst mixture, or an acid-free olefin stream is mixed with an acid-containing isoparaffin stream. In either case, a large number of venturis or mixing nozzles are often utilized to quickly disperse the olefin-containing stream into the acid-containing stream.

The resulting alkylation reaction is very exothermic and it is therefore necessary to provide means to remove the heat of reaction. This is normally done either by providing indirect heat-exchange means within the reacting mixture or by cooling one of the reactant streams, normally the acid stream, prior to passing it to the reaction zone. Mixing the acid and hydrocarbon feed stream results in the formation of an emulsion, and it is preferred that this emulsion be maintained by the continued agitation of the emulsion since this results in the removal of fluorides from the alkylate and the improvement of the octane number of the resulting alkylate. The maintenance of the emulsion is normally effected by its passage through a mixer or soak zone comprising a vessel having a number of internal obstructions which produce substantial turbulence as the emulsion passes through them. The emulsion is then typically fed into some type of settling vessel wherein a gravity separation of the emulsion is performed. The acid containing phase is removed for recirculation, and the recirculated acid may be cooled to remove the heat of reaction. The hydrocarbon phase removed from the mixer settler is passed into a fractionation column, which preferably operates as an isostripper column. This hydrocarbon phase will comprise mainly alkylate and the excess isoparaffin which was fed to the alkylation zone. Some processes do not utilize a soak zone at all and still others contact the separated hydrocarbon phase with a regenerated high strength acid stream to aid in defluorination. Further details on the design and operation of reaction vessels, the overall operation of the alkylation step, the regeneration of the preferred HF catalyst, etc., may be obtained by reference to the standard reference materials.

The net hydrocarbonaceous effluent stream of the alkylation zone is preferably passed into an isostripper column located in the fractionation zone. The isostripper recovers the $C_8$ alkylate and other $C_5$-plus hydrocarbons as a net bottoms stream removed as the product of the process. When HF is used as the alkylation catalyst, the bottoms stream contains a small amount of isopentane produced in the alkylation zone. Some propane is also produced in a $C_4$ alkylation process. A representative set of operating conditions for this column includes an overhead vapor temperature of about 60° C. and an overhead pressure of approximately 150 psig (1034 kPa g). It may contain about 65 actual trays. Preferably, the alkylation zone effluent stream enters the isostripper column at an intermediate point. Sidecut streams are preferably removed above and below the feed point. The upper sidecut carries isobutane which has passed through the alkylation zone. Preferably, this isobutane-rich stream is recycled into the alkylation zone. The lower sidecut stream will normally be rich in normal butane and is withdrawn from the alkylation unit. Since it is a lower sidecut stream, it will contain some product alkylate.

Propane, including any which is present in the feed stream(s) to the process, will enter the isostripper as part of the alkylation zone effluent stream. The propane is concentrated into the net overhead vapor of the isostripper. The overhead of the isostripper column will also contain HF and isobutane. This net overhead is preferably passed into a second column referred to in the art as a depropanizer in which the isobutane is recovered as a bottoms product. This isobutane is preferably recycled back to the alkylation zone by admixture into the upper sidecut stream of the isostripper. If there is an excess of isobutane fed to the alkylation unit, this bottoms stream is a good source of high purity isobutane and may be withdrawn from the alkylation zone after being alumina treated. The net overhead of the depropanizer comprises HF and propane and is preferably sent to a third column in which HF is stripped off as an overhead product. The HF may be returned to the alkylation zone and the propane is removed as a net bottoms product and transferred to suitable storage facilities after alumina treatment.

One embodiment of the invention may accordingly be characterized as a process for the production of an acyclic $C_8$ hydrocarbon which comprises the steps of contacting a first feed stream comprising a monohydroxyl alcohol and a second feed stream comprising a mixture of isobutane, isobutylene and normal butenes with an etherification catalyst in an etherification zone, and producing an etherification zone effluent stream which comprises a $C_4$-plus ether, the alcohol, isobutane and normal butenes; separating the etherification zone effluent stream in a fractionation column into a net bottoms stream which is rich in the ether and a net overhead stream which comprises essentially all of the isobutane and normal butenes which enter the fractionation column and which also comprises the alcohol and at least 0.3 mole percent ether; removing at least a portion of the alcohol from the net overhead stream; passing the net overhead stream into an alkylation zone in which isobutane and normal butenes are reacted in the presence of HF and the ether to produce product acyclic $C_8$ hydrocarbons; and, recovering the product $C_8$ hydrocarbons by fractionation.

What is claimed:

1. In a process for the production of an ether and a $C_8$ hydrocarbon wherein a first feed stream comprising an alcohol and a second feed stream comprising isobutylene, isobutane and normal butenes is contacted with an etherification catalyst in an etherification zone and a resultant etherification zone effluent comprising isobutane, normal butenes and a tertiary ether is produced and passed into a fractionation column, a bottoms stream comprising the ether is removed from the column, a net overhead stream comprising isobutane and normal butenes is recovered from the column, and the net overhead stream is passed into a mineral acid catalyzed alkylation zone wherein isobutane and normal butenes are reacted to produce a $C_8$ alkylate product hydrocarbon; the improvement which comprises the net overhead stream has an ether concentration above at least 0.3 mole percent.

2. A process for the production of a branched chain acyclic hydrocarbon by the alkylation reaction of a normal olefin and an isoparaffin, which process comprises the steps of:
   (a) contacting a mixture of hydrocarbons comprising a normal olefin, an isoolefin and an isoparaffin with an aliphatic alcohol in the presence of an etherification catalyst and producing an etherification zone effluent stream which comprises a $C_4$-plus tertiary ether, the normal olefin and the isoparaffin;
   (b) separating the etherification zone effluent stream within a fractionation zone into a net bottoms stream which is rich in the ether and a net overhead stream which comprises essentially all of the $C_4$ hydrocarbons present in the etherification zone effluent stream, with the net overhead stream having an ether concentration of at least 0.3 mole percent;
   (c) passing the net overhead stream into an alkylation zone in which the isoparaffin and the normal olefin are reacted in the presence of a mineral acid and the ether to produce a $C_7$-plus acyclic product hydrocarbon; and,
   (d) recovering the product hydrocarbon.

3. The process of claim 2 further limited in that the mineral acid is hydrofluoric acid.

4. The process of claim 3 further limited in that the alcohol is methanol.

5. The process of claim 3 further limited in that the ether is methyl tertiary butyl ether.

6. The process of claim 5 further limited in that the net overhead stream is passed through a methanol removal zone prior to passage into the alkylation zone.

7. A process for the production of an acyclic $C_8$ hydrocarbon which comprises the steps of:
   (a) contacting a first feed stream comprising a monohydroxyl alcohol and a second feed stream comprising a mixture of isobutane, isobutylene and normal butenes with an etherification catalyst in an etherification zone, and producing an etherification zone effluent stream which comprises a $C_4$-plus tertiary ether, the alcohol, isobutane and normal butenes;
   (b) separating the etherification zone effluent stream in a fractionation column into a net bottoms stream which is rich in the ether and a net overhead stream which comprises essentially all of the isobutane and normal butenes which enter the fractionation column and which also comprises the alcohol and at least 0.3 mole percent ether;
   (c) removing at least a portion of the alcohol from the net overhead stream;
   (d) passing the net overhead stream into an alkylation zone in which isobutane and normal butenes are reacted in the presence of HF and the ether to produce product acyclic $C_8$ hydrocarbons; and,
   (e) recovering the product $C_8$ hydrocarbons by fractionation.

8. The process of claim 7 further limited in that the ether is methyl tertiary butyl ether.

* * * * *